United States Patent
Sun et al.

(12)

(10) Patent No.: US 6,320,098 B1
(45) Date of Patent: Nov. 20, 2001

(54) CYTOPLASMIC-GENETIC MALE STERILE SOYBEAN AND METHOD FOR PRODUCING HYBRID SOYBEAN

(75) Inventors: Huan Sun; Limei Zhao; Mei Huang, all of Jilin (CN)

(73) Assignee: Jilin Academy of Agricultural Sciences, Jilin (CN)

( * ) Notice: Subject to any disclaimer, the term of this patent is extended or adjusted under 35 U.S.C. 154(b) by 0 days.

(21) Appl. No.: 09/230,958

(22) PCT Filed: May 20, 1998

(86) PCT No.: PCT/CN98/00075

§ 371 Date: Feb. 4, 1999

§ 102(e) Date: Feb. 4, 1999

(87) PCT Pub. No.: WO98/57535

PCT Pub. Date: Dec. 23, 1998

(30) Foreign Application Priority Data

Jun. 13, 1997 (CN) .................................. 97112173

(51) Int. Cl.⁷ ............................. A01H 1/02; A01H 5/00; A01H 5/10; A01H 1/04
(52) U.S. Cl. ..................... 800/274; 800/260; 800/271; 800/303; 800/312
(58) Field of Search ................................ 800/312, 303, 800/274, 271, 260, 298

(56) References Cited

U.S. PATENT DOCUMENTS 4,545,146 * 10/1985 Davis ....................................... 47/58

FOREIGN PATENT DOCUMENTS

| 1006596 | 1/1987 | (CN) . |
| 1031008 | 2/1989 | (CN) . |
| 1062635 | 7/1992 | (CN) . |

OTHER PUBLICATIONS

Dawson et al. Canadian Journal of Botany, vol. 71, pp. 629–638, 1993.*
Gai et al. Soybean Genetics Newsletter, vol. 22, pp. 55–58, (Abstract only), 1995.*
Guo et al. Soybean Genetics Newsletter, vol. 24, pp. 50, (Abstract only), 1997.*
Palmer et al. Journal of Heredity, vol. 74, pp. 260–264, 1983.*
Pei et al. Scientica Agricultura Sinica, vol. 32, pp. 32–38, (Abstract only), 1999.*
Zhao et al. Soybean Science, vol. 14, pp. 83–87, (Abstract only), 1995.*
English Abstract of CN 1006596 of Jan. 1987.
English Abstract of CN 1031008 of Feb. 1989.
English Abstract of CN 1062635 of Jul. 1992.

* cited by examiner

Primary Examiner—David T. Fox
(74) Attorney, Agent, or Firm—Ladas & Parry

(57) ABSTRACT

An improved cytoplasmic male sterile line and improved production of hybrid soybean plants which utilizes the control of a single nuclear restorer gene to impact sterility. A cytoplasmic male sterile soybean plant is provided, wherein fertility is restored through the introduction of a dominant allele at a nuclear restorer gene locus. Maintenance of the cytoplasmic male sterile soybean line is achieved through cross pollination with a male fertile isoline wherein the isoline has a fertile cytoplasm gene and recessive alleles at a nuclear restorer gene locus. The cytoplasmic male sterile line can be used as a female in the production of hybrid soybean plants when cross-pollinated with a male sterile restorer line having dominant restorer allele at the nuclear restorer gene loci. The resulting seeds are harvested from the female plant and can be planted to grow male fertile F1 plants.

7 Claims, No Drawings

CYTOPLASMIC-GENETIC MALE STERILE SOYBEAN AND METHOD FOR PRODUCING HYBRID SOYBEAN

This application is a 371 of PCT/CN98/00075 filed May 20, 1998.

FIELD OF THE INVENTION

The present invention relate to the field of plant breeding. More particularly, the invention relates to cytoplasmically male sterile soybeans, and their use in developing desirable soybean plants.

BACKGROUND OF THE INVENTION

The goal of plant breeding is to combine in a single variety or hybrid various desirable traits of the parental lines. For field crops, these traits may include resistance to diseases and insects, tolerance to heat and drought, reduced time to crop maturity, greater yield, and better overall agronomic quality. With mechanical harvesting of many crops, uniformity of plant characteristics such as germination, stand establishment, growth rate, maturity, and fruit size, is important. Plant breeding begin with the analysis and definition of problems and weaknesses of the current germplasm, the establishment of program goals and the definition of specific breeding objectives. The next step is selection of germplasm that possesses the traits to meet the program goals, and breeding to gain reproducible expression of that trait.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant. In self-pollinating species, such as soybeans and cotton, the male and female organs are anatomically juxtaposed. During natural pollination, the male reproductive organs of a given flower pollinate the female reproductive organs of the same flower. Maize can self or cross pollinate. In Brassica, the plant is normally self sterile and can only be cross-pollinated.

Soybean plants are taxonomically classified in the genus Glycine, which contains two subgenera, Glycine and Soja. Under the subgenus Soja are two species; *Glycine max*, a cultivated species, and *Glycine soja*, a wild species.

Soybean plants are recognized to be naturally self-pollinated plants which, while capable of undergoing cross-pollination, do so infrequently in nature. Insects are reported by some researchers to carry pollen from one soybean plant to another and it generally is estimated that less than one percent of soybean seed formed in an open planting can be traced to cross-pollination, i.e. less than one percent of soybean seeds formed in an open planting is capable of producing F1 hybrid soybean plants, See Jaycox, "Ecological Relationships between Honey Bees. and Soybeans," appearing in the American Bee Journal Vol. 110(8): 306–307 (August 1970). This reference and all references cited are incorporated herein by reference. Thus intervention for control of pollination is critical to establishment of superior varieties.

One of the most critical aspects of plant breeding is the ability to control the pollination process so that parental lines with desired traits are intentionally crossed to provide those same traits in the offspring.

Large scale commercial hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several options for controlling male fertility available to breeders, such as: manual or mechanical emasculation (or detasseling for maize), cytoplasmic male sterility, genetic male sterility, gametocides and the like. Most advances in male sterility have occurred with maize production.

Hybrid maize seed is typically produced by a male sterility system incorporating manual or mechanical detasseling. Alternate strips of two inbred varieties of maize are planted in a field, and the pollen-bearing tassels are removed from one of the inbreds (female) prior to pollen shed. Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed o the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled fertile maize and CMS produced seed of the same hybrid are blended to insure that adequate pollen loads are available for fertilization when the hybrid plants are grown.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 Publication No. 329, 308 and PCT application PCT/CA90/00037 published as WO 90/08828).

Another system useful in controlling male fertility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach.

Male sterility is a general phenomenon in the plant kingdom. Duvick (1966) suggested that all plant species must have at least one nuclear gene for male sterility. Laser et al. (1972) noted that there were published reports of cytoplasmic male sterility (CMS) in approximately 140 species. The number of species in which CMS has been found had greatly increased by the time of Kaul's (1988) review.

Several types of male sterile soybeans have been identified (Palmer, et al. 1987). For example, genetic male sterility (GMS), controlled by single recessive gene, has been intensively investigated and reviewed (Graybosch et al. 1988, Palmer et al. 1992). Those materials have been used in genetic studies and breeding programs such as recurrent selection.

Because of the difficulty in obtaining pure strands of male sterile plants and because of the difficulty in achieving cost-effective pollination, the use of GMS in hybrid soybean seed production is not widely practiced at present. However, the CMS system has proven to be efficient in hybrid seed production in several important crops, including maize, sorghum and rice. Cytoplasmic male sterility and restorer genes have been reported in soybeans. Davis (U.S. Pat. No. 4,545,146; U.S. Pat. No. 4,763,441, and U.S. Pat. No. 4,648,204) has disclosed cultivars which reportedly contribute male sterile cytoplasm and two pairs of recessive genes r1r1, r2r2 for male sterile maintenance. This CMS system is best described as a two gene, sporophytic system in which varieties possessing at least one allele that is dominant in each fertility restorer gene pair, R1R1 or R2R2, lead to viable pollen production even in the presence of CMS cytoplasm. There has been no reported independent verification of this system. For example, given the available seed stocks, sterility is not expressed even when the required atypical CMS cytoplasm and recessive restorer genes are present. See Davis U.S. Pat. No. 4,545,146 column 7, line 30 through column 9, line 63, where the sporophytic two- gene system is discussed.

With a sporophytic system of restoration in cytoplasmic male sterile lines, it is the genotype of the plant (sporophyte) that determines whether normal pollen is produced. Thus, a sporophytic plant that is heterozygous at a restorer gene locus produces all normal pollen even though only one-fourth of the pollen grains carry both dominant alleles. In a gametophytic system it is the genotype of the pollen grain (gametophyte) itself treat determines whether the pollen grain is normal or abnormal. Therefore such a plant that is heterozygous for a restorer gene produces one-half normal and one-half aborted pollen grains depending upon whether the dominant allele or the recessive allele is present. This is often referred to as "semi-sterility".

The invention described herein is a gametophytic, cytoplasmic male sterile soybean line. Further, unlike Davis, it requires manipulation of only one restorer gene and not two, making it easier to use in breeding.

SUMMARY OF THE INVENTION

The present invention addresses the problems presented in previously described CMS soybean systems by providing a consistently reproducible male sterile line for use in creating soybean hybrids that is relatively easy to use. It also provides for maintenance of sterility by crossing the line containing the currently described sterile cytoplasm and its recessive nuclear restorer gene with a second variety containing fertile cytoplasm and the corresponding recessive nuclear restorer gene as is in the CMS line.

Therefore, it is an object of the present invention to provide a soybean line having a gametophytic cytoplasmic male sterile system.

Another object of the invention is to provide a cytoplasmic male sterility soybean line wherein one can manipulate a single gene to control sterility. Yet another object of the invention is to provide a restorer soybean line for the cytoplasmic male sterile line described above.

It is a further object of the present invention to provide for the creation of soybean, hybrids utilizing the gametophytic cytoplasmic male sterile plant as the female parent when cross pollinated with the male fertile parent soybean plant. The female parent soybean plant will contain the sterile cytoplasm component and recessive alleles at the nuclear restorer gene specific for that cytoplasmic male sterile genetic component. The male parent described herein has at least one dominant restorer allele at the nuclear restorer gene specific for the cytoplasmic male sterile genetic component of the female parent. The hybrid soybean seeds are harvested from the female parent of this cross.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from the detailed description.

DETAILED DESCRIPTION OF THE INVENTION

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human or animal consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

The invention relates to a male sterile soybean line that is cytoplasmically male sterile and which therefore can consistently express desirable economic traits as an inbred or used as a parental line for production of hybrids. It also relates to the restorer line described.

This invention also is directed to methods for producing a soybean plant by crossing the male sterile parent soybean plant of this invention with a second parent soybean plant wherein the second parent soybean plant is a soybean plant of the line described with a homozygous dominant or heterozygous nuclear restorer gene specific for that sterile cytoplasm. Thus, any such methods using the male sterile soybean line of the invention or the restorer line are part of this invention: selfing, back-crosses, hybrid production, crosses to populations, and the like. All plants produced using a soybean variety of the invention or its male restorer line as a parent are within the scope of this invention. Advantageously, the soybean variety could be used in crosses with other, different, soybean plants to produce first generation (F1) soybean hybrid seeds and plants with superior characteristics. The variety of the invention can also be used for transformation where exogenous genes are introduced and expressed by the variety of the invention. Genetic variants created either through traditional breeding methods using the male sterile variety of the invention or through transformation of the male sterile variety of the invention by any of a number of protocols known to those of skill in the art are intended to be within the scope of this invention.

Production of a genetically modified plant tissue by transformation combines teachings of the present disclosure with a variety of techniques and expedients known in the art. In most instances alternate expedients exist for each stage of the overall process. The choice of expedients depends on the variables such as the plasmid vector system chosen for the cloning and introduction of the desired recombinant DNA molecule, as well as the particular structural gene, promoter elements and upstream elements used. Persons skilled in the art are able to select and use appropriate alternatives to achieve functionality. Culture conditions for expressing desired structural genes and cultured cells are known in the art. Also as known in the art, soybeans are transformable and regenerable such that whole plants containing and expressing desired genes under regulatory control may be obtained. General descriptions of plant expression vectors and reporter genes and transformation protocols can be found in Gruber, et al., "Vectors for Plant Transformation", in Methods in Plant Molecular Biology & Biotechnology, Glich et al., (Eds. pp. 89–119, CRC Press, 1993).

Moreover GUS expression vectors and GUS gene cassettes are available from Clone Tech Laboratories, Inc., Palo Alto, Calif., while luciferase expression vectors and luciferase gene cassettes are available from Pro Mega Corp. (Madison, Wis.). General methods of culturing plant tissues are provided for example by Maki et al., "Procedures for Introducing Foreign DNA into Plants" in Methods in Plant Molecular Biology & Biotechnology, Glich et al. (Eds. pp. 67–88 CRC Press, 1993); and by Phillips et al., "Cell-Tissue Culture and In-Vitro Manipulation" in Corn & Corn Improvement, $3^{rd}$ Edition, Sprague et al. (Eds. app. 345–387 American Society of Agronomy Inc., 1988.) Methods of introducing expression vectors into plant tissue include the direct infection or co-cultivation of plant cells with *Agrobacterium tumefaciens*, Horsch et al., Science, 227:1229 (1985). Descriptions of Agrobacterium vector systems and methods for Agrobacterium-mediated gene transfer provided by Gruber, et al. supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device. One example is that described at European Patent 30,749. Transformant plants obtained with the protoplasm of the invention are intended to be within the scope of this invention.

As used herein, the term plant includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, and the like.

Further reproduction of the variety can occur by tissue culture and regeneration. Tissue culture of various tissues of soybeans and regeneration of plants therefrom is well known and widely published. For example, reference may be made to Komatsuda, T. et al., "Genotype X Sucrose Interactions for Somatic Embryogenesis in Soybean," Crop Sci. 31:333–337 (1991); Stephens, P. A. et al., "Agronomic Evaluation of Tissue-Culture-Derived Soybean Plants," Theor. Appl. Genet. 82:633–635(1991); Komatsuda, T. et al., "Maturation and Germination of Somatic Embryos as Affected by Sucrose and Plant Growth Regulators in Soybeans *Glycine gracilis* Skvortz and *Glycine max* (L.) Merr.," Plant Cell, Tissue and Organ Culture, 28:103–113 (1992); Dhir, S. et al., "Regeneration of Fertile Plants from Protoplasts of Soybean (*Glycine max* L. Merr.): Genotypic Differences in Culture; Response," Plant Cell Reports 11:285–289(1992) Pandey, P. et al., "Plant Regeneration from Leaf and Hypocotyl Explants of *Glycine wightii* (W. and A.) VERDC var longicauda," Japan J. Breed. 42:1–5 (1992); and Shetty, K., et al., "Stimulation of In Vitro Shoot Organogenesis in Glycine max (Merrill.) by Allantoin and Amides," Plant Science 81:245–251(1992) as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference.

It is well known in the art that cytoplasm genetics are inherited in most plants, including soybeans, through the female parent only. In these plants, pollen does not transmit a cytoplasm component. This invention provides for a male sterile soybean plant having a sterile cytoplasm wherein the cytoplasm genetic component is for a sterile (S) cytoplasm. This male sterile soybean plant further has recessive alleles (rf x rf x ) at the nuclear restorer gene locus specific for that cytoplasm. This combination of (S) cytoplasm and (rf x rf x) genotype for the restorer gene confers a male sterile phenotype to the plant. This male sterile phenotype can be maintained and can be further exploited in the creation of F1 hybrid soybean seed.

The male sterile soybean line, described herein, having cytoplasmic genotype (S) and nuclear restorer genotype (rf x rf x ) can be maintained by cross-pollination with the male fertile isoline described (maintainer line) having, a fertile, or normal, cytoplasmic genotype (F) and the (rf x rf x) nuclear restorer genotype. The female parent (male sterile line) is referred to as the A-line. The male parent (male fertile line) is referred to as either the B-line or the maintainer line. This seed harvested from the female parent inherits the cytoplasmic genotype (S) from the female. The remainder of the genotype is essentially the same for the male and female parent, thus, the seed harvested from the female parent plant is the same genetically as the female parent plant itself —including the cytoplasmic male sterility.

In the present invention, the mode of restoration is gametophytic. In other words, it is the genotype of the pollen grain, or gametophyte, that determines whether the pollen is normal or abnormal. A genotype of Rf x rf x at the restorer gene locus, in the presence of sterile (S) cytoplasm, will result in 50% fertile pollen and 50% sterile or aborted pollen. Buchert, J.G., "The state of genome-plasmon interaction in the restoration of fertility to cytoplasmically pollen sterile maize", Proc. Natl. Acad. Sci. USA 47:1426–1440. (1961).

This invention further provides for the production of hybrid soybeans through cross-pollination by utilizing the male sterile soybean plant described herein as the female parent and the line carrying at least one dominant restorer allele as the male parent, also described. Seed is harvested from the female parent and used to grow F1 hybrid soybean plants.

In the preferred embodiment of this invention, the cytoplasmic male sterile plant is created by a cross of *Glycine max*, line '167', as the female parent and *Glycine soja*, line '035', as the male parent. *Glycine max*, line '167', with its specific sterile cytoplasm (S) genetic component is restored to fertility by dominant fertility alleles (Rf x Rf x) at the nuclear restorer locus specific for that sterile cytoplasm genetic component. *Glycine soja*, line '035', has fertile cytoplasm (F) and carries the recessive alleles (rf x rf x) at the nuclear restorer locus for the specific cytoplasm carried in line '167'. In addition, *Glycine soja*, line '035', carries a homozygous translocation (T/T), resulting in a higher than expected percent pollen sterility in the progeny. The seeds are harvested from the female plant, planted and upon maturity, self-pollinated to create a F2 population. From this F2 population, plants carrying the (rf x rf x) genotype are selected and used as a female parent in a series of back-crosses with *Glycine soja*, line '035'. From the back-cross progeny select progeny with a high percentage sterile pollen grains and interchanged chromosomes (T/T). The resulting genotype for cytoplasm:nucleus is S: (rf x rf x) (T/T). At least five backcross cycles were completed. The resulting progeny can be crossed to either the B-line for maintaining seed source for hybrid production or to any restored soybean line as described above. In addition, the use of genetic traits, such as flower or pubescence color, tightly linked to the restorer gene could act as a phenotypic marker in the field. Of course, the *G. Soja* phenotype cannot be directly used in hybrid production because of its unacceptable agronomic characteristics. But it can be readily crossed with the cultivated types of soybean to result in the desired parental lines after sufficient backcrossing.

It should be emphasized that in the creation of hybrid soybean lines, both manual cross-pollination and insect-mediated cross pollination can be used. Manual intermating is difficult and time consuming, therefore, not practical for commercial production. Insect-mediated cross-pollination, using bees for example, is more conducive to commercial production. The male sterile plant of this invention is used as the female parent and the restored line is used as the male parent. The insects carry the pollen from the male parent plant to the female parent, thus cross-pollinating the plant. The seed is then harvested from the female parent. Several methods are known in the art for increasing the attractiveness of the flowering soybean plants to bees, such as limiting rainfall or irrigation during flowering to increase nectar flow, selecting plants with a larger blossom size or the presence of an odor attractive to insects such as bee sex pheromones.

The concept of the invention described herein allows for the controlled growth of soybean hybrids. These hybrids will allow for the increased yields and other benefits of increased heterosis arid hybrid vigor.

EXAMPLE 1

Materials and Methods

Experiments were initiated to investigate chromosome translocation frequency of *G. soja* and to identify possible combinations showing interaction of male sterile cytoplasm and sterile maintaining gene(s). Six sites in China, located at Gongzhuling, Jilin; Zhengzhou, Henan; Xuzhou, Jiangsu; Hang zhou, Zhejiang; Changsha, Hunan and Quanzhou, Fujian, were chosen to grow experimental materials. The wide range of geographic distribution of those sites, covering from 25 to 44 degrees north latitude, provided the opportunity to select experimental samples on a broad genetic basis. 133 varieties of *G. max* and 213 collections of *G. soja* came from different maturity groups and could mature normally at one of the above-mentioned six sites. These varieties were used as female and male parents respectively in the crosses.

The genotypes of both *G. max* and *G. soja* were screened to present the greatest genetic diversities. For instance, the female cultivated parents were composed of landrace as well as modem cultivars. Both typical annual wild soybean and semi-wild soybean were included in male parents.

376 cross combinations of *G. max* by *G. soja* were made during the experimental time period. F1 seeds produced from most combinations were grown in a photoperiod-controlled room at Gongzhuling, Jilin; some were grown in Zhengzhou, Henan. The fertility of pollen grains of F1 plants were checked by 12-KI staining and the percentage of sterile pollen grains was calculated. Abortions in the pod weighing less than 28 milligrams were considered to be either aborted ovules or early seed abortion.

Results and Discussion

Palmer et al (1976, 1984) confirmed that the semi-sterility of F1 pollen grains from crosses of *G. max* by *G. soja* were due to a chromosome translocation in *G. soja*. Spontaneous translocation was found to be rare in *G. max*. Taking *G. max* as a common non-translocation parent, as high as 59.6% of 213 combinations of *G. max* X *G. soja* used in this study had translocated chromosomes. This result was not surprising. Delannay et al (1982) checked 19 samples of *G. soja* collections from China for frequency of translocation and found that 16 of them (i.e. 84%) had a suspected translocation.

A specific cross of *G. max* line 'Ru Nan Tian E Dan' (It is called '167'in this invention) by *G. soja* line '5090035' (It is called '035' in this invention) was found to have extremely high pollen grain sterility of 88.01 % in F1 plants. To exclude the possibility induced by accidental factors such as experimental errors or unfavorable growing conditions, two additional crosses including reciprocal ones were made. The results of pollen checking are listed in Table 1.

TABLE 1

Pollen Fertilities of F1 Plants From Reciprocal Crosses '167' x '035' and Their Parents

| Year of Cross Made | Combination | Growing Condition of F1 Plants | Percentage of Sterile Pollen of F1 (%) |
| --- | --- | --- | --- |
| Year 1 | '167' x '035' | Photo-controlled in GZ* | 88.01 |
| Year 3 | '167' x '035' | Photo-controlled in GZ* | 92.70 |
| Year 3 | '035' x '167' | Photo-controlled in GZ* | 58.44 |
| Year 3 | '167' | Field in ZZ** | 2.38 |
| Year 3 | '035' | Field in ZZ** | 2.17 |
| Year 5 | '167' x '035' | Field in ZZ** | 88.37 |

*Gongzhuling, Jilin,
**Zhengzhou, Henan

The data in Table 1 demonstrates that the pollen fertility of parents '167' and '035' was normal. The high degree of pollen sterility found in F1 plants of '167'x'035' could be repeated in different years and different growing conditions. The average percentage of sterile pollen grains were 89.69% in three years with a very low difference of 4.69% between the highest and the lowest value. It clearly demonstrated that genetic causes were responsible for the sterility.

The semi-sterility of F1 plants in cross '035'x'167' is believed to result from the involvement of chromosome translocation in one of the two parents. Considering the high frequency of translocation in *G. soja*, line '035' was suspected to have one chromosome translocated. A modern soybean cultivar 'ZhengZhou 64-1', which appears to have no translocation, was chosen as common parent to cross with '035' and '167' respectively to test and verify these suppositions. The results in Table 2 indicated that the semi-sterility of pollen grains in F1 plants appeared in reciprocal crosses in which line '035' was included but not in crosses having line '167' as a parent. Therefore the possibility of chromosome translocation in '167' could be eliminated.

TABLE 2

Pollen Fertilities of F1 Plants From Crosses of 'Zhengzhou 64-1' by '035' and '167'

| Year of Cross Made | Combination | Growing Condition of F1 Plants | Percentage of Sterile Pollen of F1 (%) |
| --- | --- | --- | --- |
| Year 3 | 'Zhengzhou 64-1' × '035' | Photo-controlled in GZ* | 55.60 |
| Year 3 | × '035' × 'Zhengzhou 64-1' | Photo-controlled in GZ* | 54.95 |
| Year 5 | 'Zhengzhou 64-1' × '167' | Field in ZZ** | 0.26 |
| Year 5 | '167' × 'Zhengzhou 64-1' | Field in ZZ** | 3.04 |

*Gongzhuling, Jilin,
**Zhengzhou, Henan

Heterozygotes for a chromosome translocation should also cause semi-aborted ovules. The percentage of aborted ovules in the F1 plants of 'Zhengzhou 64-1×035' and '035×Zhengzhou 64-1' were 43.00% and 35.78% compared to those of 7.03% and 6.74% in '167' and '035' respectively. Beiling (1915) stated that in Stizolobium sp., pods with all ovules aborted abscised. The same situation is believed to happen in soybean. If those aborted ovules within the pods possibly abscised were added to the observed abortion ovules, the percentage of aborted ovules would be close to 50%. Both semi-sterile pollen and semi-aborted ovules in F1 of crosses involving 035 confirmed the existence of translocation in *G. soja* line of '035'.

The reciprocal crosses resulted in different percentages of sterile pollen in F1 plants. Percent sterile pollen was 32.26% higher in the positive cross of '167'×'035' than that in the negative cross of '035'×'167' (Table 1). The effects of '167' cytoplasm on the fertility of F1 plants were obviously revealed and such effects were found to be true only when line '035' nuclear genome was in '167' cytoplasm. The interaction of '167' cytoplasm with '035' nuclear gene(s) predicted the possibility of obtaining a cytoplasmic-nuclear male sterile line. The nuclear substitution backcrosses were initiated in 1990. Three BC1F1 plants were obtained in 1991. The percent of sterile pollen in each BC1F1 plants was 99.93%., 93.53% and 99.27% respectively. The second backcross was conducted and 0, 1, 10 BC2F1 seeds were harvested from the three BC1F1 plants respectively. All BC2F1 seeds were planted in greenhouse in winter 1991 and four BC2F1 plants derived from the same BC1F1 plant were obtained. The only BC2F1 seed harvested from another BC1F1 plant failed to germinate.

The whole backcross procedure is illustrated as follows:

| Year | Location | Cross Procedure | Average Percentage of Sterile Pollen (%) |
| --- | --- | --- | --- |
| Year 5 summer | Zhengzhou | '167' × '035' | |
| Year 6 summer | Zhengzhou | F1 × '035' | 88.38 |
| Year 7 summer | Zhengzhou | BC1F1 × '035' | 97.58 |
| Year 7 winter | Gongzhuling | BC2F1 × '035' | 99.57 |
| Year 8 summer | Zhengzhou | BC3F1 × '035' | 99.93 |
| Year 9 summer | Zhengzhou | BC4F1 × '035' | 99.93 |
| | | BC5F1 × '035' (A-line)(B-line) | |

The continuous backcrosses were ended in summer of Year 9 and highly male sterile plants, the CMS A-line, and its maintainer, the male fertile B-line, were obtained. CMS A-line and B-line obtained here with *G. soja* phenotype will be called OA and OB, respectively, hereafter in this invention.

Some important characteristics of OA are described below:

Morphology: The OA and OB had typical phenotype of annual wild soybean with vining stem, small leaves, and black seeds weighing 2.5 g/100 seeds. OA and OB have an indeterminate type of stem termination, gray pubescence, and white flowers with purple throats. The OA was similar to its maintainer OB morphologically except for delayed leaf senescence at maturity, few pods set, and large amounts of unfertilized small pods ranging from 0.5–1.0 cm on mature plants.

Micrograph of pollen grain: Light microscopy showed the pollen grains of OA were small, with the diameter of 17.15 $\mu$m compared to 21.73 $\mu$m of normal pollen in OB. The wall of the pollen appeared well developed but the content was shrunken. The pollen could not be stained by 12-K1 and was light brown.

Male sterile stability: The BC4F1 plants were used to grow in three conditions with different treatments of photoperiod regimes and temperatures. The male sterility remained stable and at a very high level. The growing conditions were as follows:

Year 8 winter: The plants were grown in the greenhouse in Gongzhuling. Twenty four hours of light were given for two weeks and then reduced Year 8 winter: The plants were grown in the greenhouse in Gongzhuling. Twenty four hours of light were given for two weeks and then reduced to 13.5 hours till flowering. The temperature was variable due to an unstable heating system. The percentage of sterile pollen was 97.95%.

Year 9 summer: The plants were grown in the fields in Zhengzhou. They were planted in early June and flowered in early August. The temperature kept very high all over the growing season. Pollen sterility was 99.93%.

Year 9 summer: Plants also were grown in a photo-controlled room in Gongzhuling. Light was provided for 14 hours after emergence until full pod setting. The temperature was low during the planting time in early May and was increased during flowering time in early July. The percentage of sterile pollen was 99.94%.

The data indicated that the percentage of sterile pollen grains of CMS plants remained almost the same in highly varied environments, and also revealed that the male sterility was quite stable.

Female Fertility: A common parent of '167' was used to cross to OA and OB at the same time. The success rates of crosses (i.e. the pod setting rates) were used to estimate female fertility. The parallel crosses were done by the same person to reduce the artificial experimental error to the lowest level. The results are shown in Table 3.

TABLE 3

Results of Female Fertility Test

| Cross Combination | No. of Cross Made | No. of Pod Setting | Success Rates |
|---|---|---|---|
| OA × '167' | 123 | 33 | 26.82 |
| OB × '167' | 123 | 35 | 28.46 |

The pod setting rate on OA was just 1.64% lower than that on OB. The significance test revealed no difference between the two cases at the 0.01 level. The female of OA seemed normal.

The distinct difference of male sterility of F1s between reciprocal crosses '167'×'035' and '035'×'167', and the maintenance of high level male sterility after continuous nuclear substitution back-crosses, could only be explained by the cytoplasmic-nuclear male sterile system. Without intending to be limited by theory, we tentatively suppose that the combination of sterile cytoplasm S in the '167' line and a pair of recessive restorer genes rf x rf x in the '035' line (i.e. S(rf x rf x)) caused the male sterility in CMS OA. The mode of genetic control in the OB and line '167' should be N(rf x rf x) and S(Rf x Rf x) respectively. However, the high level of male sterility in the F1 of '167'×'035' may need explanation. One explanation, without intending to be limited by theory, is that the involvement of a chromosome translocation in the '035' line may have caused semi-sterility in the F1 of '167'×'035' due to the heterozygous translocation (T/N). However, the ratio of plants with the heterozygous translocation would be expected to be reduced to $\frac{1}{32}$ in the BC5 population. Alternatively, the restorer gene Rf x may have been incompletely dominant to rf x. This has been found in CMS systems in other species. Other alternative possibilities include that this CMS system is a gametophytic type, in which the heterozygote of Rf x rf x produced semi-sterile pollen grains, or, finally, that the nuclear gene(s) responsible for male sterility was dominant. These possible explanations (except chromosome translocation) can be confirmed by more precise genetic studies, but again, the inventor(s) do not intend to be limited by theory.

The CMS OA and OB have the phenotype of *G. soja*, which contributed the nuclear genome in recurrent back-crosses. As previously described, it could not be used directly in hybrid soybean production due to its unacceptable agronomic characteristics. However, the CMS male sterile system can be easily expanded to cultivated types of soybean. The key point is that *G. soja* and *G. max* are closely related species, and there is virtually no barrier to gene flow between them. In fact, gene transfer from one to another has frequently been practiced in conventional breeding programs without any obstacles.

EXAMPLE 2

*G.soja* is believed to be the ancestor of *G. max*. Most of its agronomic characters are not acceptable to modern agriculture. Therefore the cytoplasmic male sterile line OA having the phenotype of *G.soja* described herein in this invention can not directly be used in hybrid soybean production. As mentioned above there is no specific barrier between *G.soja* and *G.max* and any forms of intermating between them can be practiced. It is well known in the art that several ways are available for the transfer of cytoplasmic male sterile genetic components existing in *G.soja* line OA to *G.max*. One of them is test- crosses to screen for the cytoplasmic male sterile component carried in the nuclear genome in *G.soja* line OB among *G.max* soybean. In other words, the test-crosses are used to screen among *G. max* for the recessive gene rf x rf x at the nuclear restorer locus in OB that could maintain the male sterility in OA.

In Example 1 of this invention, the BC3F1 (It will be called OABC3 in the following description) of the back-crosses of ('167'×'035')×'035' was obtained in year 8. Its percentage of sterile pollen grains was as high as 99.93%. The test-crosses were carried out by taking OABC3 as female ]parent and a number of *G.max* as male parents. The followings were the procedures of test-cross and back-crosses with a soybean variety 'Yi Chuan Lu Da Dou' as male parent.

| Year | Location | Cross Procedure | Average Percentage of Sterile Pollen (%) |
|---|---|---|---|
| Year 8 Summer | Zhengzhou | OABC3 X 'Yi Chuan lu Da Dou' | |
| Year 8 Winter | Gongzhuling | F 1X 'Yi Chuan lu Da Dou' | 99.00 |
| Year 9 Summer | Zhengzhou | BC11F1 X 'Yi Chuan lu Da' | 99.05 |
| Year 9 Winter | Gongzhuling | BC2F1 X 'Yi Chuan lu Da Dou' | 99.92 |
| Year 10 Summer | Zhengzhou | BC3F1 X 'Yi Chuan lu Da Dou' | 99.95 |
| Year 10 Winter | Gongzhuling | BC4F1 X 'Yi Chuan lu Da Dou' BC5F1 'Yi Chuan lu Da Dou' A-line     B-line | 99.95 |

A new CMS A-line was obtained by continuous back-crossing OABC3 with 'Yi Chuan Lu Da Dou'. The new CMS A-line and its maintainer B-line. 'Yi Chuan lu Da Dou' will be called YA and YB hereafter in this invention. Both YA and YB have a typical cultivated soybean phenotype. The chromosome translocation in *G.soja* OA and OB was eliminated in YA and YB after five cycles of backcrosses.

EXAMPLE 3

The following shows the results of pollen fertility measured in four populations of a three way testcross in Table 4. S.P.G. refers to the percent of sterile pollen that was measured and F, SS, S refer to fertile, semi-sterile and sterile respectively. Note that the female parent is on the left and male parent is on the right. All of the data were collected in the Henan province, where the lines originated from.

YA is a *Glycine max* which is cytoplasmically male sterile and with recessive alleles of its nuclear restorer gene (S-rf x rf x). YB is a *Glycine max* line which has fertile cytoplasm with recessive alleles at the same nuclear restorer gene (F-rf x rf x). Line '167' has a sterile cytoplasm genetic component and has been restored to fertility through the homozygous dominant alleles of its nuclear restorer gene (S-Rf x Rf x).

In the first column, there are shown results of YA, crossed with a F1 from a cross between line '167' and YB. The genetics are expected to be S-rf x rf x (YA), crossed with S-Rf x rf x ('167' x YB). Note that in the case of this male, only Rf-carrying pollen grains will be viable because of the cytoplasm from line '167'. The results of this cross are progeny that are expected to show 50% sterility, with their genetics being S-Rf x rf x. Note here that since line '167' has game-tophytic cytoplasmic sterility, and not sporophytic cytoplasmic sterility, pollen grains resulting from the '167' X YB F1 carrying the recessive restorer allele will be nonviable.

This explains the results of 50% sterility. As noted below, the ratio of fertile progeny to semi-sterile progeny to sterile progeny is 0:10:1. The one sterile plant is believed to result from what has been well documented instances of cytoplasmic reversions to fertility that enables a recessive restorer allele to be transmitted. In these cases, reversions to fertility are expressed by development of pollen grains carrying the recessive rf-allele. When this occurs, fully male-sterile progeny plants can develop (S-rf x rf x). In maize, frequency of this is dependent upon genotype. (Gabay-Laughnam, S., G. Zabala, J. R., "S-Type Cytoplasmic Male Sterility in Maize", pp. 395–432. In Ch. S. Levings III and I.K. Vasil (eds)., "The Molecular Biology of Plant Mitochondria", Kuwar Academic Publishers, Netherlands. (1995))

In the second column are the results of crossing YA with a F1 resulting from YB crossed with the 167 line. Here the genetics involved are S-rf x rf x by F-Rf x rf x with a 1:1 ratio predicted consisting of progeny that are S-rf x Rf x and S-rf x rf x. In this case, both the Rf x allele and the rf x allele are transmitted because the original F1 was carrying fertile cytoplasm. As can be seen, the number of fertile progeny to semi-sterile progeny to sterile progeny is 0:19:16, and thus is reflective of the expected 1:1 ratio of semi-sterile to sterile progeny plants.

In the third column, a F1 is made by crossing YA with the '167' line, resulting in progeny that are S-Rf x rf x. This is used as female parent in a cross with YB. Progeny are once again expected to segregate 1:1 for semi-sterile: sterile plants as both the Rf x allele and the rf x alleles are viable through the female. The two fertile plants can be explained by instances of cytoplasmic reversions to fertility, as described above.

In the fourth column, a cross between a F1 of the '167' line and YB with YB, should result in a 1:1 segregation of semi-sterile to sterile progeny. As can be observed, the ratio is actually closer to 2:1 of semi-sterile to sterile progeny. These results may be explained by examining a similar phenomenon in maize observed by Gabay-Laughnan, Zabala, and Laughnan (1995). These authors observed a phenomenon in which pollen is produced that looks and stains as normal but that is non-functional. As of the date of publication, they observed seven independent occurrences of this in four different inbred lines. In the soybean example, therefore, some of the apparent semi-sterile plants could actually be functionally sterile plants, even though they have a normal pollen grain staining appearance. If not for this phenomenon, they would have been classified as all sterile plants.

TABLE 4

Pollen Fertility in Four Populations of Three Way Test Crosses

| % S.P.G. | YABC5 X (167XYB) | YABC5 X (YBX167) | (YABC5X167) XYB | (167XYB)XYB |
|---|---|---|---|---|
| 1–10 | 0 | 0 | 2 | 5 |
| 10.1–20 | 0 | 0 | 0 | 0 |
| 20.1–30 | 0 | 0 | 0 | 0 |
| 30.1–40 | 0 | 0 | 0 | 2 |
| 40.1–50 | 4 | 5 | 2 | 4 |
| 50.1–60 | 5 | 9 | 7 | 22 |
| 60.1–70 | 1 | 5 | 1 | 1 |
| 70.1–80 | 0 | 0 | 0 | 0 |

TABLE 4-continued

Pollen Fertility in Four Populations of Three Way Test Crosses

| % S.P.G. | YABC5 X (167XYB) | YABC5 X (YBX167) | (YABC5X167) XYB | (167XYB)XYB |
|---|---|---|---|---|
| 80.1–90 | 0 | 0 | 0 | 0 |
| 90.1–100 | 1 | 16 | 7 | 14 |
|  | F:SS:S | F:SS:S | F:SS:S | F:SS:S |
|  | 0:10:1 | 0:19:16 | 2:10:7 | 5:29:14 |

Pollen fertility in two F2 populations was also measured, and as can be seen in Table 5 below, the first a cross between YA and the '167' line, and the second a cross between the '167' line and YB. These results also reflect the genetics involved. In the YA x '167' F2 population the genetics are a S-rf x rf x by a S-Rf x Rf x resulting in a S-Rf x rf x. The F2 generation then would be 1:1 of S-Rf x Rf x and S-rf x Rf x with one half fertile and one half semi-sterile progeny. In the second cross of 167 by YB, the results are expected to be S-Rf x rf x and in the F2 generation, S-Rf x Rf x , S-rf x Rf x, with again a 1:1 ratio between fertile and semi-sterile progeny. Here again, the 6 sterile progeny in the first cross and the 7 sterile progeny in the second cross can be explained despite the genetics involved, by cytoplasmic reversions, as described above. Many factors can enter into the results which are practically obtained from crosses between two known genetic lines. Environment is a factor, as are the anomalies mentioned above where in a gametophytic system the recessive allele is transmitted by the female. Taking these practical considerations into mind, one can see that the data ere shows convincingly the one gene gametophytic system involved here. Once gain without intending to be limited by theory, the inventors emphasize that there may be the possibility of modifier gene(s) in some of the genetic materials, but these modifiers are still compatible with the gametophytic single gene system described herein.

This confirms that the system is manipulated through a gametophytic single gene, as opposed to the sporophytic double gene system of Davis. It should be noted that soybean is a diploidized polyploid and that multiple genes can relate to a particular trait; however, they are typically quiescent. In any event, with this invention only one nuclear gene needs to be controlled to impact sterility. As is evident to one skilled in the art this makes genetic manipulation through crossing, backcrossing, or the like considerably easier.

TABLE 5

Pollen Fertility in two F2 Populations

| % of S.P.G. | (YA x 167) F2 | (167 x YB) F2 |
|---|---|---|
| 0–10 | 111 | 115 |
| 10.1–20 | 4 | 1 |
| 20.1–30 | 7 | 6 |
| 30.1–40 | 22 | 8 |
| 40.1–50 | 42 | 27 |
| 50.1–60 | 31 | 58 |
| 60.1–70 | 2 | 3 |
| 70.1–80 | 2 | 0 |
| 80.1–90 | 0 | 0 |
| 90.1–100 | 6 | 7 |
|  | F:SS:S | F:SS:S |
|  | 111:110:6 | 115:103:7 |

EXAMPLE 4

The sterility trait in the instant invention is stable throughout tested temperature and photoperiod changes. Table 6 shows the percent of sterile pollen grains over varying photoperiods.

Temperatures were varied as shown in Table 7, where the first temperature shown is the daytime temperature and the second is the nighttime temperature, with three variations shown. As can be seen, the sterility remained highly stable in the face of such fluctuations.

TABLE 6

Percentage of Sterile Pollen Grain of OA at Different Photoperiods When Day-Night Temperature Regime was Set at 30–20° C.

| Materials | Replication | Photoperiod (hours) | | |
|---|---|---|---|---|
| | | 12.5 | 14.0 | 15.5 |
| OA | 1 | 99.92 | 99.94 | 99.80 |
| | 2 | 99.96 | 99.96 | 99.70 |
| | 3 | 99.69 | 99.79 | 99.65 |
| Average | | 99.82 | 99.90 | 99.72 |

TABLE 7

Percentage of Sterile Pollen Grains of OA at Different Day-Night Temperature Regime When Photoperiod was Set at 14.0 Hours

| Materials | Replication | Temperature (° C.) | | |
|---|---|---|---|---|
| | | 25–15 | 30–20 | 35–25 |
| OA | 1 | 99.91 | 99.65 | 99.85 |
| | 2 | 100.00 | 99.78 | 99.75 |
| | 3 | 99.93 | 99.85 | 99.60 |
| Average | | 99.94 | 99.76 | 99.93 |

Applicants have made a deposit of at least 2500 seeds each of 'A' (OA S(rfrf)), 'B' or '035' (OB (5090035), F(rfrf)), and '167' (Ru Nan Tian E Dan, S(RfRf) with the China Center for Type Culture Collection (CCTCC), Wuhan, Hubei, 430072 pursuant to the Budapest Treaty, CCTCC Deposit Nos. P97002, P97003, and P97004, respectively. The seeds deposited with the CCTCC on Nov. 17, 1997 were taken from the deposit maintained by Jilin Academy of Agricultural Sciences, Gongzhuling, Jilin, 136100, China since prior to the filing date of this application. The above named deposits will be maintained in the CCTCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§1.801–1.809, including providing an indication of the viability of the sample. At the time of indication of allowability, Applicants impose no restrictions on the availability of the deposited material from the CCTCC; however, Applicants have no authority to waive any restrictions imposed by law on the transfer of biological material or its transportation in commerce. Applicants do not waive any infringement of its rights granted under this patent.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims. All references cited herein are hereby incorporated herein by reference.

REFERENCES

1. BEILING, G., 1915. Linkage and semi-sterility. American Nature, 49:582–584.
2. DAVIS, W. H., 1985. Route to hybrid soybean production. U.S. Pat. No. 4,545,146.
3. DELANNAY, X., KILEN, T. C., PALMER, R.G., 1982. Screening of soybean (G. max) accessions and G. soja accessions for chromosome interchange and inversions. Agronomy abstract, American Society of Agronomy, Madison, Wis. pp. 63.
4. DUVICK, D. N., 1966. Inference of morphology and Sterility on breeding methodology. In "Plant Breeding", pp. 85–138. Ed. FREY, K.J., A symposium held at Iowa State University Press, Ames.
5. GRAYBOSCH, R. A. and PALMIER, R. G., 1988. Male sterility in soybean —An overview. American Journal of Botany. 75(1):144–156.
6. KAUL, M. L. H., 1988: Male sterility in higher plant. Monographs on Theor. and Appl. Genet. Vol. 10. Springer-Verlag, Berlin.
7. LASER, K. D. and LERSTEN, N. R., 1972. Anatomy and cytology of microsporogenesis in cytoplasmic male sterile angiosperms. Botanical Review, Vol. 38, No. 3, 425–454.
8. PALMER, R. G., 1976. Cyto genetics in soybean improvement. Proc. Sixth Soybean Res. Conf., American Seed Trade Assoc. Publ. 6:55–66.
9. PALMER, R. G., ALBERTSEN, M. C., HORNER, H. T. and SKORUPSKA, H., 1992. Male sterility in soybean and maize: developmental comparisons. The Nucleus, Vol. 35(1), 1–18.
10. PALMER, R. G. and HEER, H., 1984. Agronomic characteristics and genetics of a chromosome interchange in soybean. Euphytica, 33:651–653.
11. PALMER, R. G. and KILEN, T. C., 1987. Qualitative genetics and cytogenetics. In "Soybeans: improvement, production and uses", 135–209, Ed. Wilcox, J. R., American Society of Agronomy, No. 16, Madison, Wis., U.S.A.

Although the invention has been described with preferred embodiments, it is to be understood that variations and modifications may be resorted to as will be apparent to those skilled in the art. Such variations and modifications are to be considered within the purview and scope of the claims appended hereto.

What is claimed is:

1. A cytoplasmic male sterile soybean plant, or its parts, produced by repetitively back-crossing the F1 progeny of a cross of G. max 'Ru Nan Tian E Dan', representative seed of which is deposited at CCTCC accession No. P97004, as a female parent and G. soja '5090035', representative seed of which is deposited at CCTCC accession No. P97003, as a male parent, wherein the F1 progeny seed from the female parent is harvested and back-crossed with G. soja '5090035' as a back-cross male parent, and selecting for male sterile progeny at the back-cross generations.

2. A male fertile soybean plant, or its parts, containing a cytoplasmic male sterile genetic component, said component being that found in G. max 'Ru Nan Tian E Dan', representative seed of which is deposited at CCTCC accession No. P97004, and dominant alleles of a nuclear restorer gene which confers male fertility in the presence of said cytoplasmic male sterile genetic component.

3. A method for producing a cytoplasmically male sterile soybean plant; the method comprising repetitively back-crossing the F1 progeny of a cross of G. max 'Ru Nan Tian E Dan', representative seed of which is deposited at CCTCC accession No. P97004, as a female parent and G. soja '5090035', representative seed of which is deposited at CCTCC accession No. P97003, as a male parent, wherein the F1 progeny seed from the female parent is harvested and back-crossed with *G. soja* '5090035' as the back-cross male parent, and selecting for male sterile progeny at the back-cross generations.

4. A male fertile soybean plant, or its parts, having a homozygous recessive nuclear restorer gene of *G. soja* '5090035', representative seed of which is deposited at CCTCC accession No. P97003, capable of allowing expression of male sterility in the presence of the male sterile cytoplasm of *G. max* 'Ru Nan Tian E Dan', representative seed of which is deposited at CCTCC accession No. P97004.

5. A cytoplasmic male sterile soybean plant, or its parts, having a homozygous recessive cytoplasm specific nuclear restorer gene capable of allowing expression of male sterility in the presence of a male sterile cytoplasm of *G. max* 'Ru Nan Tian E Dan', representative seed of which is deposited at CCTCC accession No. P97004, and further having the male sterile cytoplasm found in *G. max* 'Ru Nan Tian E Dan'.

6. A method for producing hybrid soybean comprising:

crossing as a female parent a cytoplasmic male sterile soybean plant comprising a male sterile cytoplasm found in *G. max* 'Ru Nan Tian E Dan', representative seed of which have been deposited at CCTCC accession No. P97004, and a homozygous recessive cytoplasm specific nuclear restorer gene capable of allowing expression of male sterility in the presence of said male sterile cytoplasm found in *G. max* 'Ru Nan Tian E Dan' with a male parent soybean plant comprising dominant alleles of a cytoplasm specific nuclear restorer gene capable of conferring male fertility in the presence of the male sterile cytoplasm found in *G. max* 'Ru Nan Tian E Dan'; and harvesting hybrid F1 seeds from the female parent.

7. A method of identifying a male fertile soybean plant comprising a homozygous recessive cytoplasm specific nuclear restorer gene capable of allowing expression of male sterility in the presence of male sterile cytoplasm found in *G. max* 'Ru Nan Tian E Dan', representative seed of which have been deposited at CCTCC accession No. P97004, the method comprising:

crossing as a female parent a male sterile soybean plant known to comprise the male sterile cytoplasm found in *G. max* 'Ru Nan Tian E Dan' and a homozygous recessive cytoplasm specific nuclear restorer gene capable of allowing expression of male sterility in the presence of said male sterile cytoplasm found in *G. max* 'Ru Nan Tian E Dan' with a male fertile soybean plant, whose said cytoplasm specific nuclear restorer gene zygosity is unknown, as a male parent;

harvesting seed from said female parent;

growing plants from said harvested seed;

observing pollen from said grown plants and determining if pollen from all grown plants is aborted, fertile, or both; and identifying said male fertile parent soybean plant wherein all said grown progeny plants exhibit only aborted pollen.

* * * * *